(12) United States Patent
Abbas et al.

(10) Patent No.: US 8,323,952 B2
(45) Date of Patent: Dec. 4, 2012

(54) **ALCOHOLIC XYLOSE FERMENTATION AT HIGH TEMPERATURES BY THE THERMOTOLERANT YEAST *HANSENULA POLYMORPHA***

(75) Inventors: Charles A. Abbas, Champaign, IL (US); Andriy A. Sibirny, Lviv (UA); Andriy Y. Voronovsky, Lviv (UA); Olena P. Ishchuk, Lviv (UA)

(73) Assignee: Archer Daniels Midland Company, Decatur, IL (US)

( * ) Notice: Subject to any disclaimer, the term of this patent is extended or adjusted under 35 U.S.C. 154(b) by 858 days.

(21) Appl. No.: 12/330,839

(22) Filed: Dec. 9, 2008

(65) Prior Publication Data
US 2009/0155872 A1  Jun. 18, 2009

Related U.S. Application Data

(60) Provisional application No. 61/007,477, filed on Dec. 13, 2007.

(51) Int. Cl.
*C12N 1/00* (2006.01)
*C12N 1/19* (2006.01)

(52) U.S. Cl. .................... 435/255.1; 435/254.2
(58) Field of Classification Search .............. None
See application file for complete search history.

(56) References Cited

U.S. PATENT DOCUMENTS

| | | | |
|---|---|---|---|
| 6,551,829 B1 | 4/2003 | Takano et al. | |
| 7,045,290 B2 * | 5/2006 | Lindquist et al. | 435/6.16 |
| 2006/0228789 A1 | 10/2006 | Jeffries et al. | |
| 2008/0254524 A1 * | 10/2008 | Abbas et al. | 435/161 |

OTHER PUBLICATIONS

GenBank accession No. AY550078, 2011.*
Sibirny et al. Abstract for The 29th Symposium on Biotechnology for Fuels and Chemicals (Apr. 29-May 2) 2007.*
International Preliminary Report on Patentability for PCT/US2008/086041 dated Jun. 24, 2010 (Forms PCT/IB/326, PCT/IB/373, & PCT/ISA/237).
International Search Report dated Mar. 25, 2009.
Newnam et al., "Antagonistic Interactions between Yeast Chaperones Hsp104 and Hsp70 in Prion Curing", Molecular and Cellular Biology, Feb. 1999, p. 1325-1333, vol. 19, No. 2.
Dmytruk et al., "Overexpression of Bacterial Xylose Isomerase and Yeast Host Xylulokinase Improves Xylose Alcoholic Fermentation in the Thermotolerant Yeast *Hansenula polymorpha*", FEMS Yeast Res., 2008, p. 165-173, vol. 8.

* cited by examiner

*Primary Examiner* — Michele K Joike
(74) *Attorney, Agent, or Firm* — Mark W. Roberts

(57) ABSTRACT

Methods and compositions for the production of ethanol from lignocellulosic starting materials are provided herein. Embodiments provide yeast cells of the genus *H. polymorpha* with one or more modifications, including, for example, an inactive acid trehalase gene, overexpression of xylulokinase, and/or overexpression of heat-shock protein 104.

9 Claims, 1 Drawing Sheet

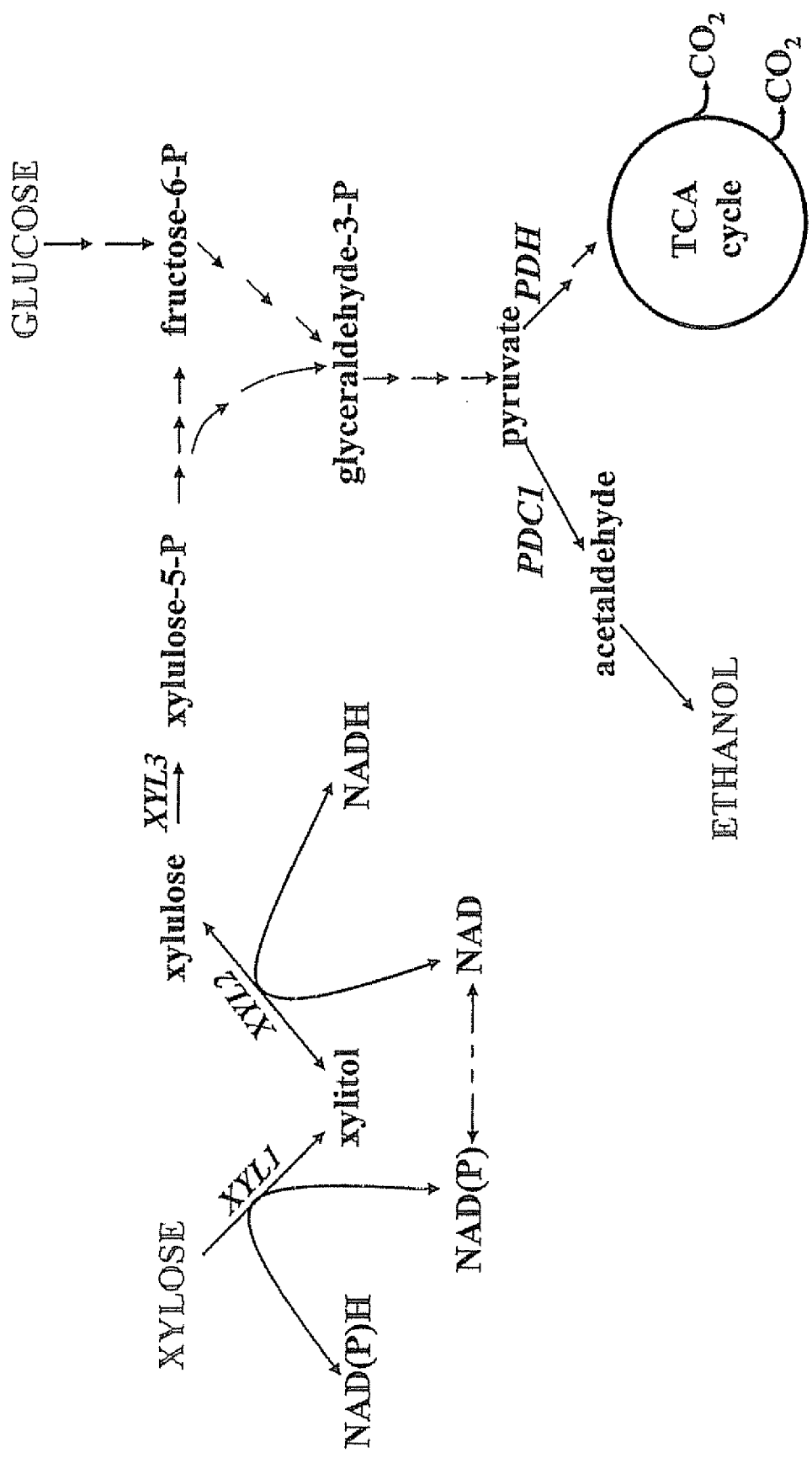

ALCOHOLIC XYLOSE FERMENTATION AT HIGH TEMPERATURES BY THE THERMOTOLERANT YEAST *HANSENULA POLYMORPHA*

CROSS-REFERENCE TO RELATED APPLICATION

This application claims priority to pending U.S. Provisional Patent Application Ser. No. 61/007,477, filed on Dec. 13, 2007. U.S. Provisional Patent Application Ser. No. 61/007,477 is incorporated by reference into this application as if fully rewritten herein.

BACKGROUND OF THE INVENTION

1. Field of the Invention

Embodiments presented herein relate to methods and compositions for the fermentative production of ethanol from D-xylose using yeast.

2. Background

Metabolic engineering of microorganisms is often an effective means to produce commercially a number of chemicals that may be used for multiple applications (see, e.g., Lee, S. Y., et al. *Macromol. Biosci.* 4:157-164 (2004)). One chemical that has garnered much interest is ethanol. Although ethanol has a number of uses, it is most commonly used as fuel. As a fuel, ethanol is a low value product with much of the cost of its production attributed to the cost of raw materials. It would be desirable, therefore, to develop ethanolgens and fermentation processes for the production of ethanol from readily available, inexpensive starting materials. These starting materials may be, for example, lignocellulosics. These lignocellulosics may be derived, for example, from renewable biomass waste streams from food, paper pulping operations, agricultural residues and recycled paper from municipalities.

Lignocellulose is approximately 30% D-xylose (see Ryabova, O. B., et al. "Xylose and Cellobiose Fermentation to Ethanol by the Thermotolerant Methylotrophic Yeast *Hansenula polymorpha*," *FEMS Yeast Res.* 4:157-164 (2003)). Xylose is a "wood sugar" with the IUPAC designation (2S,3R,4S,5R)-oxane-2,3,4,5-tetrol.

Only a relatively small number of wild type microorganisms can ferment D-xylose. These microorganisms are generally not suitable for large-scale fermentation. This unfavorability may arise, for example, as a result of unfamiliarity with the microorganisms, difficulty obtaining the microorganisms, poor productivity and/or growth on pretreated lignocellulosics or unsatisfactory yield when grown on mixed sugars derived from biomass. C. Abbas, "Lignocellulosics to ethanol: meeting ethanol demand in the future," The Alcohol Textbook, 4$^{th}$ Edition. (K. A. Jacques, T. P. Lyons and D. R. Kelsall, eds). Nottingham University Press, Nottingham, UK, 2003, pp. 41-57; Cite 2 C. Abbas, "Emerging biorefineries and biotechnological applications of nonconventional yeast: now and in the future," The Alcohol Textbook, 4$^{th}$ Edition. (K. A. Jacques, T. P. Lyons and D. R. Kelsall, eds). Nottingham University Press, Nottingham, United Kingdom, 2003, pp. 171-191.

Yeasts are considered the most promising microorganisms for alcoholic fermentation of xylose (see Ryabova, supra). They have larger cells than bacteria, are resistant to viral infection, and tend to be more resistant to negative feedback from ethanol. Furthermore, yeast growth and metabolism have been extensively studied for a number of species. A number of yeasts are known to naturally ferment D-xylose. These include *Pichia stipitis, Candida shehatae*, and *Pachysolen tannophilus* (see Ryabova, supra; C. Abbas 2003). The common brewer's yeast *Saccharomyces cerevisiae* is not known to ferment D-xylose naturally, but a number of strains of biologically engineered *S. cerevisiae* that do ferment D-xylose have been reported.

As shown in FIG. 1, D-Xylose metabolism in yeast is has been reported to proceed along a pathway similar to that of glucose via pentose phosphate pathway. Carbon from D-xylose is processed to ethanol via the glycolytic cycle or to CO2 via respiratory TCA cycle It has been proposed that one bottleneck involved in D-xylose fermentation is the hydrolysis of xylan, which is the major component of hemicellulose to monosaccharides (see Ryabova, supra). One approach to overcoming this bottleneck is by using "simultaneous saccharification and fermentation" (SSF). This is a process in which pretreated lignocellulose is hydrolyzed by cellulases and hemicellulases while the hexoses and pentoses produced by this hydrolysis (including xylose) are fermented to ethanol. This would allow continuous conversion of the sugars to ethanol, preventing their accumulation in the medium.

A potential drawback of SSF is the difference in the optimal temperature at which cellulases and hemicellulases are active (at least about 50° C.) that are compatible with the optimal temperature for yeast growth and fermentation of xylose (about 30° C.). One solution to this potential drawback is to perform SSF using the thermotolerant methylotrophic yeast *Hansenula polymorpha* (also known as *Pichia angusta*). This yeast has been reported to have optimum and maximum growth temperatures of 37° C. and 48° C., respectively. These temperatures are higher than those tolerated by most other ethanol producing yeasts (Ryabova, et al.). Furthermore, Ryabova, et al. reported that under some conditions *H. polymorpha* is able to naturally ferment D-xylose (see also Voronovsky, A. Y., et al., "Expression of xylA Genes Encoding Xylose Isomerases From *Escherichia coli* and *Streptomyces coelicolor* in the Methylotrophic Yeast *Hansenula polymorpha*" *FEMS Yeast Res.* 5(11): 1055-62 (2005)). Behavior of *H. polymorpha* under high temperatures is reported, for instance, in Escalante, J., et al., "Biomass Production by a Thermotolerant Yeast: *Hansenula polymorpha*" *J. Chem. Tech. Biotechnol.* 48: 61-70 (1990); Tsiomenko, A. B., et al., "Secretory Heat-Shock Protein of the Thermotolerant Yeast *Hansenula polymorpha*. Identification and Comparative Characteristics" *Biochemistry (Moscow)* 62(2): 123-128 (1997); Lindquist, S. & Kim, G., "Heat-shock Protein 104 Expression is Sufficient for Thermotolerance in Yeast" *Proc. Natl. Acad. Sci. USA* 93: 5301-5306 (1996); Guerra, E., et al. "Hypoxia Abolishes Transience of the Heat-shock Response in the Methylotrophic Yeast *Hansenula polymorpha*" *Microbiology* 151: 805-811 (2005).

Therefore it would be advantageous to develop strains of *H. polymorpha* with an increased ability to produce ethanol from lignocellulosic starting materials, including the C5 sugar, D-xylose. The present teachings may provide these advantages and/or others, and may provide further advantages that one of skill in the art will readily discern from the detailed description that follows.

SUMMARY OF THE INVENTION

The present teaching describes several different features and aspects of the invention with reference to various exemplary embodiments. It is understood, however, that the invention embraces numerous alternative embodiments, which may be accomplished by combining any of the different features and aspects described herein in any combination that one of ordinary skill in the art would find useful.

Provided herein are genes and genetic elements useful in modifying host cells. These host cells may include, for example, microorganisms. One particularly suitable microorganism for use in embodiments of the invention is the yeast *H. polymorpha*. Methods and compositions of the invention are useful for providing microorganisms with increased enzyme activity. In one embodiment, an *H. polymorpha* host cell overexpresses the *H. polymorpha* heat-shock protein 104. In a further embodiment, an *H. polymorpha* cell having a deletion of the ATH1 (acid trehalase) gene is provided. The ATH1 deletion improves thermotolerance and tolerance to ethanol, resulting in an increase of ethanol production. In a further embodiment, a strain of *H. polymorpha* overexpresses xylulokinase (XYL3). In a yet still further embodiment, a strain of yeast of the invention has at least two of the following properties: (a) the yeast overexpresses heat-shock protein 104; (b) the yeast has an inactive ATH1 gene; and (c) the yeast overexpresses xylulokinase.

A further embodiment provides processes for production of ethanol by fermenting one or more strains of yeast of the invention.

BRIEF DESCRIPTION OF THE SEVERAL VIEWS OF THE DRAWINGS

FIG. 1 is a scheme of xylose and glucose metabolism in yeasts.

DETAILED DESCRIPTION OF THE INVENTION

As used herein, the singular forms "an," "a," and "the" used in the specification and claims include both singular and plural unless the content clearly dictates otherwise. In particular, those skilled in the art will recognize that while design and creation of catalytic materials and catalytic supports are described in terms of a single cell, more effective systems will include one or more cells each expressing one or more receptor proteins.

Provided herein are methods and compositions of matter useful in one or more of increasing thermotolerance and decreasing feedback inhibition by ethanol in ethanol-producing yeasts, typically in members of the *Hansenula* (*Pichia*) genus, and most typically in *H. polymorpha* (*P. angusta*). Novel strains are provided. Methods of ethanol production using strains of the invention are also provided.

It is to be understood that certain descriptions of the embodiments of the invention have been simplified to illustrate only those elements and limitations that are relevant to a clear understanding of the present invention, while eliminating, for the purposes of clarity, other elements. Those of ordinary skill in the art, upon considering the present description, will recognize that other elements and/or limitations may be desirable to implement embodiments of the invention. Because such other elements and/or limitations may be ascertained by one of ordinary skill in the art upon considering the present description, and are not necessary for a complete understanding of the embodiments, a discussion of such elements and limitations is not provided herein. Still, the description set forth herein is not intended to limit the scope of the claims.

By the term "gene" is meant a segment of nucleic acid, DNA or RNA, which encodes and is capable of expressing a specific gene product. A gene often produces a protein or polypeptide as its gene product, but in its broader sense, a gene can produce any desired product, whether the product is a protein, polypeptide or nucleic acid. Functional or structural nucleic acid, such as, without limitation, rRNA, ribozymes, antisense RNA or interfering RNA (e.g., siRNA) also may be considered "gene products."

A "gene" contains an "expressed sequence" that can encode not only a protein or polypeptide, but a structural or functional nucleic acid, such as an antisense or siRNA. A gene may also contain sequences containing regulatory elements, such as, without limitation, promoters, enhancers and terminators; such regulatory elements may be "operably linked," most typically in an appropriate proximity to each other. Such promoters operate in cis (attached to each other on the same nucleic acid molecule) to cause expression of "a gene product." The choice of gene constituents, such as the particular combination of regulatory elements and expressed sequence, will dictate the conditions of expression. For example, a constitutive promoter, such as the TEF1 (translation elongation factor 1A gene) promoter, coupled to an expressed sequence will cause constitutive expression of the expressed sequence when transferred into a suitable host cell. A "constitutive promoter" is an unregulated promoter that allows for continual transcription of its associated gene. A promoter is considered constitutive if it functions to promote transcription of a gene under normal growth conditions. A constitutive promoter typically is not substrate specific and does not vary substantially in its expression under normal growth conditions.

A "gene" can include introns or other DNA sequences that can be spliced from the final RNA transcript. An expressed DNA sequence that encodes a protein or peptide ("protein encoding sequence") includes an open reading frame (ORF). The protein encoding sequence may comprise intervening introns. Further, the term "gene" includes expressed sequences as well as non-expressed sequences. All DNA sequences provided herein are understood to include complementary strands unless otherwise noted. Furthermore, RNA sequences can be prepared from DNA sequences by substituting uracil for thymine, and are included in the scope of this definition and invention, along with RNA copies of the DNA sequences of the invention isolated from cells.

By the term "oligonucleotide" is meant a nucleic acid of from about 7 to about 50 bases though they are more typically from about 15 to about 35 bases. Oligonucleotides are useful as probes or primers for use in hybridization or amplification assays such as Southern or Northern blots; molecular beacon; polymerase chain reaction (PCR); reverse transcriptive PCR (RT-PCR); quantitative RT-PCR (QRT-PCT), e.g., TAQ-MAN; isothermal amplification methods, such as NASBA (nucleic acid sequence-based amplification); and rolling circle amplification, including use of padlock probes. Oligonucleotides of the invention can be modified by the addition of peptides, labels (including fluorescent, quantum dot, or enzyme tags), and other chemical moieties and are understood to be included in the scope of this definition and the invention.

As used herein, in the context of the novel nucleotide sequences described herein, a nucleic acid is "specific to" a given sequence, such as the pyruvate decarboxylase cDNA and genomic sequences provided, if it can hybridize specifically to a given sequence under stringent conditions, such as, without limitation, 0.2×SSC at 65° or in a PCR reaction under typical reaction (annealing) temperatures. Typically, one sequence is "specific" to a reference sequence if the nucleic acid has 90 to 100% homology (sequence identity) to the reference sequence.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches. Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) CABIOS 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, as modified in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mouth View, Calif.); the ALIGN program (Version 2.0) and GAP, BESTFIT, BLAST, FASTA, and TFASTA in the CGC Wisconsin Genetics Software Packages, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244; Higgins et al. (1989) CABIOS 5:151-153; Corpet et al. (1988) *Nucleic Acids Res.* 16:10881-90; Huange et al. (1992) CABIOS 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra.

BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=5, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, and PSI-BLAST, the default parameters of the respective programs (e.g., BLASTN for nucleotide sequences, BLASTX for proteins) can be used. See the National Center for Biotechnology Information web site on the world wide web at ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nswgapdna.cmp scoring matrix; or any equivalent program thereof.

By "equivalent program" is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts.

If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Packages for protein sequences are 8 and 2, respectively. For nucleotide sequences, the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Packages is BLOSUM62 (see Henikoff and Henikoff (1989) *Proc. Natl. Acad. Sci. USA* 89: 10915).

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, typically at least 80%, more typically at least 90%, and most typically at least 95%, compared to a reference sequence using one of the alignment programs described using standard parameters.

In the context of the sequences provided herein, a sequence is specific to that reference sequence if, under any given reaction condition that can be used to distinguish one sequence from another, such as, without limitation, PCR, Southern blot or Northern blot, but not to other sequences, such as sequences from other species including without limitation those of *S. cerevisiae, A. niger, A. terreus, P. pastoris*, and *S. pombe*. Thus, in a nucleic acid detection assay, a probe/primer is "specific to" a sequence if it can bind to a specific transcript or desired family of transcripts extracted from a specimen, to the practical inclusion (i.e., does not interfere substantially with the detection assay) of other sequences. In a PCR assay, primers are specific to a reference sequence if they specifically amplify a portion of that sequence, to the practical exclusion of other sequences in a sample.

As used herein, a "primer" or "probe" for detecting a specific nucleic acid species is any primer, primer set, and/or probe that can be utilized to detect and/or quantify the specific nucleic acid species. A "nucleic acid species" can be a single nucleic acid species, corresponding to a single gene, or can be nucleic acids that are detected by a single common primer and/or probe combination.

By the term "host cell" is meant any prokaryotic or eukaryotic cell where a desired nucleic acid sequence has been introduced into the cell. The metabolic processes and pathways of such a host cell are capable of maintaining, replicating, and/or expressing a vector containing a foreign gene or DNA molecule. There are a variety of suitable host cells, including but not limited to bacterial, fungal, insect, mammalian, and plant cells, that can be utilized in various ways (for example, as a carrier to maintain a plasmid comprising a desired sequence). Representative microbial host cells include, but are not limited to, fungal cells such as *Rhizopus* sp., *Saccharomyces* sp., *Streptomyces* sp., *Pichia* sp., *Aspergillus* sp., and bacterial cells such as *Lactobacillus* sp., *Escherichia* sp., *Corynebacterium* sp., *Brevibacterium* sp., *Pseudomonas* sp., *Proteus* sp., *Enterobacter* sp., *Citrobacter* sp., *Erwinia* sp., *Xanthomonas* sp., *Flavobacterium* sp., *Streptococcus* sp., *Lactococcus* sp., *Leuconostoc* sp., and *Enterococcus* sp. In one embodiment, the host cell is *Hansenula polymorpha* (*Pichia angusta*). In another embodiment, the host cell is *Escherichia coli*. In a yet still further embodiment, the host cell is *Saccharomyces cerevisiae*.

By the term "polynucleotide" is meant any single-stranded sequence of nucleotide, connected by phosphodiester linkages, or any double-stranded sequences comprising two such complementary single-stranded sequences held together by hydrogen bonds. Unless otherwise indicated, each polynucleotide sequence set forth herein is presented as a sequence of deoxyribonucleotides (abbreviated A, G, C and T). The term "polynucleotide" encompasses DNA molecules or polynucleotide, sequences of deoxyribonucleotides, and RNA molecules or polyribonucleotides and combinations thereof.

By the term "promoter" is meant a DNA sequence within a larger DNA sequence that provides or defines a site to which RNA polymerase can bind and initiate transcription. The promoters described herein can be used to over-express or up-regulate, for example, and without limitation, genes encoding enzymes that increase carbon flux to lactic acid, fumarate, and other desired metabolites during changes in fermentation conditions.

An "equivalent" of a given reference nucleotide sequence or element contained therein is a nucleotide sequence containing, as compared to the reference nucleotide sequence, all elements of that reference nucleotide sequence, such that the characteristic function of that reference nucleic acid or peptide is retained. Those of skill in the art understand that a functional protein may be encoded by equivalent DNA sequences due to degeneracy in the genetic code. For example, one codon may be substituted for another, yet encode the same amino acid, such as, for example and without limitation, in reference to the Ala codon, the substitution of GCG for GCA. In the case of proteins, a sequence can contain amino acids that represent conservative amino acid substitutions, including but not limited to, the conservative substitution groups: Ser and Thr; Leu, Ile and Val; Glu and Asp; and Gln and Asn. A sequence as claimed herein thus includes the referenced sequence as well as its equivalents due to degeneracy in the genetic code. Conservative substitutions also can be determined by other methods, such as, without limitation, those used by the BLAST (Basic Local Alignment Search Tool) algorithm, the BLOSUM Substitution Scoring Matrix, and the BLOSUM 62 matrix (see also, for example, Altschul et al., *Methods in Enzymology* 266:460-479 (1996)). Importantly, "equivalents" and "conserved equivalents" of a reference nucleic acid or peptide/protein substantially retain or enhance the function of the reference nucleic acid or peptide/protein.

By the term "vector" is meant a means for introducing a foreign nucleotide sequence into a cell, including without limitation, a plasmid or virus. Such vectors can operate under the control of a host cell's gene expression machinery. A vector contains sequences that facilitate replication and/or maintenance of a segment of foreign nucleic acid in the host cell. Generally, the vector is introduced into a host cell for the replication and/or expression of the segment of foreign DNA or for delivery of the foreign DNA into the host genome. A typical plasmid vector contains: (i) an origin of replication, so that the vector can be maintained and/or replicated in a host cell; (ii) a selectable marker, such as an antibiotic resistance gene to select cells containing the vector (transformants) among vectorless cells, and (iii) a polylinker site containing several different restriction endonuclease recognition and cut sites to facilitate cloning of a foreign DNA sequence.

Provided herein are genes and genetic elements useful in modifying host cells. These host cells may include, for example, microorganisms. One particularly suitable microorganism for use in embodiments of the invention is the yeast *H. polymorpha* (*P. angusta*). Methods and compositions of the invention are useful for providing microorganisms with increased enzyme activity.

Methods and compositions provided herein may be particularly useful for fermentative production of ethanol using SSF (simultaneous saccharification and fermentation). Strains of the invention may also be particularly suited for fermentative production of ethanol at high temperatures. By "high temperatures" it is meant, for instance, fermentation conducted at temperatures between 40 and 60° C., between 40 and 55° C., between 40 and 50° C., between 45 and 55° C., between 45 and 50° C., between 48 and 52° C., and between 48 and 50° C. Typical temperatures for fermentation include 48° C. and 50° C.

I. STRAINS AND METHODS FOR PRODUCING ETHANOL FROM D-XYLOSE USING *H. polymorpha* THAT OVERPRODUCES *H. polymorpha* HEAT-SHOCK PROTEIN 104

In one embodiment of the invention an ethanol-producing yeast of the species *H. polymorpha* is provided, wherein the yeast has been modified to have an increased production of ethanol in a medium having D-xylose as a primary carbon source by increasing the expression amount of the *H. polymorpha* heat-shock protein 104 in the yeast. In examples reported herein the ethanol production is relative to that of a control strain that is a *H. polymorpha* transformant NCYC495 leu 1-1 (ScLEU2). The transformant is a derivative of strain NCYC495 leu 1-1 containing the *S. cerevisiae* LEU2 gene. In other embodiments the increased production is relating to that of a parent strain of *H. polymorpha*.

Production of ethanol may also be increased by increasing the expression amount of a protein that has an amino acid sequence with one or more deletions, substitutions, insertions, inversions, or additions to the amino acid sequence of *H. polymorpha* heat-shock protein 104, wherein said protein is at least 90%, at least 95%, at least 98%, or at least 99% identical to the wild-type *H. polymorpha* heat-shock protein 104.

In one embodiment, the expression of heat-shock protein 104 is increased by increasing the copy number of the *H. polymorpha* heat-shock protein 104 gene (HSP104) (in a strain of *H. polymorpha*. In a further embodiment, HSP104 is placed under the control of a non-native promoter. The non-native promoter may be, for example, but is not limited to, a constitutive promoter. In one embodiment, the non-native promoter is the promoter of the GAPDH (glyceraldehyde-3-phosphate dehydrogenase) gene of *H. polymorpha*.

The copy number of the HSP104 gene may be increased, for example, by transforming a parent strain of *H. polymorpha* with a plasmid carrying the ORF of the HSP104 gene, or by transforming a parent strain of *H. polymorpha* with a plasmid carrying the ORF of the HSP104 gene under the control of the GAPDH promoter. The promoter is selected from, for example, promoters of the GAPDH, PMA1 (Plasma membrane H+-ATPase), TEF1 (translation elongation factor 1A), and PGK1 (3-phosphoglycerate kinase) genes. Those skilled in the art will recognize a number of ways to transform *H. polymorpha* with the desired gene or gene/promotor construct.

Yeasts with increased expression of the heat-shock 104 protein may be cultured in a D-xylose-containing medium to produce ethanol. A method of providing ethanol according to an embodiment of the invention comprises the steps of cultivating yeast with increased expression of heat-shock 104 protein in a D-xylose-containing culture medium to ferment D-xylose, accumulating ethanol in the medium, and collecting ethanol from the medium. The fermentation may be conducted in the presence of 12% xylose at a temperature of 48-50° C. over a time period of 1-3 days at semiaerobic conditions (140 rpm).

The fermentation was conducted in minimal medium (YNB) with xylose; xylose concentrations were 4 to 12%; the best ethanol production was at 12% xylose. pH was approx. 3 to 5 and was checked periodically. "Improved growth" means better biomass accumulation at increased temperature (50° C.). OD was measured at 600 nm. In all presented experiments the *H. polymorpha* transformant NCYC495 leu 1-1 (ScLEU2) was used as a control strain. This transformant was used as a control strain because all tested recombinant strains (HSP104-8, Δath1-36, Δath1-36_XYL3) were obtained after transformations by vectors carrying the ScLEU2. Thus, the tested strains contained the gene (ScLEU2). The strain Δath1-36_XYL3 was deposited on Sep. 13, 2007, in the NRRL ARS Culture Collection, Peoria, Ill., USA, under the terms of the Budapest Treaty, as deposit no. NRRL Y-50061.

II. STRAINS AND METHODS FOR PRODUCING ETHANOL FROM D-XYLOSE USING *H. polymorpha* LACKING AN ACTIVE ATH1 (ACID TREHALASE) GENE In one embodiment of the invention an ethanol-producing yeast of the species *H. polymorpha* is provided, wherein the yeast has been modified to have increased production of ethanol on D-xylose by inactivation of the ATH1 (acid trehalase) gene. The acid trehalase gene in the yeast *Saccharomyces cerevisiae* is discussed by Jung, Y-J. & Park, H-D. "Antisense-mediated Inhibition of Acid Trehalase (ATH1) Gene Expression Promotes Ethanol Fermentation and Tolerance in *Saccharomyces cerevisiae*" Biotech. Lett. 27: 1855-1859 (2005); and Kim, J., et al. "Disruption o the Yeast ATH1 Gene Confers Better Survival after Dehydration, Freezing, and Ethanol Shock: Potential Commercial Applications" *Appl. & Envir. Microbiol.* 62(5): 1563-1569 (1996).

The terms "ATH1 gene inactivated," "inactive ATH1 gene," "inactivation of the ATH1 gene," and the like mean that the ATH1 gene is modified such that the gene encodes a mutant protein. The mutant protein may have decreased activity or it may be entirely inactive. The ATH1 gene may also have been modified such that it is unable to provide the natural expression of acid trehalase protein due to deletion of all or part of the ATH1 gene, modification of regions adjacent to the ATH1 gene, or disruption of one or more parts of the ATH1 gene by addition of one or more nucleotides to the ATH1 gene.

Those skilled in the art will recognize, with the benefit of this disclosure, a number of ways to inactivate the ATH1 gene in *H. polymorpha*. These include, for example, but are not limited to, disruption, partial or complete deletion of the gene.

Yeasts in which the ATH1 gene has been inactivated may by further modified to enhance ethanol production at desired conditions. For example, the expression of one or more genes involved in ethanol production may be enhanced. One or more genes in the yeast may be inactivated to optimize allocation of carbon resources to fermentation.

Yeasts in which the ATH1 gene is inactive may be wild-type *H. polymorpha* or they may be strains of *H. polymorpha* in which ethanol production on D-xylose has already been increased beyond that of wild-type *H. polymorpha*. Yeasts may be further modified to increase ethanol production on D-xylose according to other embodiments of the invention.

Yeasts with an inactive ATH1 gene may be cultured in a D-xylose-containing medium to produce ethanol. A method of providing ethanol according to an embodiment of the invention comprises the steps of cultivating yeast with an inactive ATH1 gene in a D-xylose-containing culture medium to ferment D-xylose, accumulating ethanol in the medium, and collecting ethanol from the medium. The fermentation may be conducted in the presence of 12% xylose at a temperature of 48-50° C. over a time period of 1-3 days at semi-aerobic conditions (140 rpm).

The fermentation was conducted in minimal medium (YNB) with xylose; xylose concentrations were 4 to 12%; the best ethanol production was at 12% xylose. pH was approx. 3 to 5 and was checked periodically. "Improved growth" means better biomass accumulation at increased temperature (50° C.). OD was measured at 600 nm. In all presented experiments the *H. polymorpha* transformant NCYC495 leu 1-1 (ScLEU2) was used as a control strain.

III. STRAINS AND METHODS FOR PRODUCING ETHANOL FROM D-XYLOSE USING *H. polymorpha* THAT OVERPRODUCES XYLULOKINASE In one embodiment of the invention an ethanol-producing yeast of the species *H. polymorpha* is provided, wherein the yeast has been modified to have an increased production of ethanol in a medium having D-xylose as a primary carbon source by increasing the expression amount of the *H. polymorpha* protein xylulokinase in the yeast. In one embodiment the increased ethanol production is relative to that of a control strain that is a wild-type *H. polymorpha*, and in another embodiment the increased production is relative to that of a parent strain of *H. polymorpha*.

Production of ethanol may also be increased by increasing the expression amount of a protein that has an amino acid sequence with one or more deletions, substitutions, insertions, inversions, or additions to the amino acid sequence of *H. polymorpha* xylulokinase, wherein said protein is at least 90%, at least 95%, at least 98%, or at least 99% identical to the amino acid sequence of wild-type *H. polymorpha* xylulokinase.

In one embodiment, the expression of xylulokinase is increased by increasing the copy number of the *H. polymorpha* xylulokinase gene (XYL3) in a strain of *H. polymorpha*. In a further embodiment, XYL3 is placed under the control of a non-native promoter.

The non-native promoter may be, for example, but is not limited to, a constitutive promoter. In one embodiment, the non-native promoter is the promoter of the GAPDH (glyceraldehyde-3-phosphate dehydrogenase) gene of *H. polymorpha*. The promoter is selected from, for example, promoters of the GAPDH, PMA1 (Plasma membrane H+-ATPase), TEF1 (translation elongation factor 1A), PGK1 (3-phosphoglycerate kinase) genes.

The copy number of the XYL3 gene may be increased, for example, by transforming a parent strain of *H. polymorpha* with a plasmid carrying the ORF of the XYL3 gene under the control of the GAPDH promoter (GenBank #AY550078). The copy number of the HSP104 gene may be increased, for example, by transforming a parent strain of *H. polymorpha* with a plasmid carrying the ORF of the HSP104 gene under the control of the GAPDH promoter (GenBank #AY550078). Those skilled in the art will recognize a number of ways to transform *H. polymorpha* with the desired gene or gene/promotor construct.

Yeasts with increased expression of xylulokinase may be cultured in a D-xylose-containing medium to produce ethanol. A method of providing ethanol according to an embodiment of the invention comprises the steps of cultivating yeast with increased expression of xylulokinase in a D-xylose-containing culture medium to ferment D-xylose, accumulating ethanol in the medium, and collecting ethanol from the medium. The fermentation may be conducted, for example, in the presence of 12% xylose at a temperature of 48-50° C. over a time period of 1-3 days at semiaerobic conditions (140 rpm).

IV. ADDITIONAL EMBODIMENTS

In a further embodiment of the invention, one or more of the aspects described in Section I, Section II, and Section III may be used in combination to provide a strain of *H. polymorpha* with increased ethanol production on D-xylose. For example, one embodiment may provide a strain of *H. polymorpha* in which the ATH1 gene is inactive but the XYL3 gene is overexpressed and/or has an increased copy number. Another embodiment may provide a strain of *H. polymorpha* with an inactive ATH1 gene, overexpression and/or increased copy number of the XYL3 gene, and overexpression and/or increased copy number of the HSP104 gene. Yet another embodiment provides a strain of *H. polymorpha* with overexpression and/or increased copy number of the XYL3 gene and with increased copy number and/or overexpression of the HSP104 gene. Still another embodiment of the invention provides a strain of *H. polymorpha* with an inactive ATH1 gene and increased copy number and/or overexpression of the HSP104 gene.

Those skilled in the art will, with the benefit of this disclosure, recognize that further modifications may be made to host cells of the invention, which allow for further nutritional requirements altered production of ethanol and/or other chemicals. For example, one may produce a strain of *H. polymorpha* suitable for ethanol production in a medium in which D-xylose is the primary energy source by any combination of increased expression of heat-shock protein 104, inactivation of ATH1, and increased expression of xylulokinase. Modifications that are already known to those skilled in the art, as well as modifications that are later developed, may be used in addition to those taught herein.

Strains and Plasmids

Microbial strains and plasmids used in embodiments of the invention are provided in Table 1.

TABLE 1

| | Description | Source |
|---|---|---|
| Strains | | |
| H. polymorpha NCYC495 leu1-1 (ATCC MYA-335) | leu2, deficient in β-isopropyl malate dehydrogenase | ATCC, USA |
| HSP104-8 | derivative of NCYC495 leu1-1 with HSP104 under GAPDH control | This Disclosure |
| Δath1-36 | derivative of NCYC495 leu1-1 with deletion of the ATH1 (acid trehalase) gene | This Disclosure |
| Δath1-36_XYL3 | derivative of Δath1-36 with deletion of the ATH1 (acid trehalase) gene and with an additional HpXYL3 gene under GAPDH control | This Disclosure |
| Plasmids | | |
| pKO8 + prGAP + HSP104Hp | ORF of the *H. polymorpha* HSP104 (heat-shock protein 104) gene under the control of the GAPDH gene promoter | This Disclosure |
| pΔATH1HP | plasmid for deletion of ATH1 gene | This Disclosure |
| pXYL3 | plasmid for addition of *H. polymorpha* xylulokinase XYL3 gene driven by GAPDH promoter. | This Disclosure |

Media and Culture Conditions

Media and culture conditions used in experiments for embodiments of the invention are as provided below, unless they are stated as otherwise in specific examples. Yeasts are grown in synthetic yeast nitrogen-base (YNB) medium supplemented with xylose as sole carbon and energy source (2%) at 37° C. Liquid-medium cultivations were conducted in 40 ml of the medium with 12% xylose in 125-ml Erlenmeyer shake flasks at a shaker at 37 or 48° C. Oxygen-limited conditions were provided by agitating at 135-140 rpm. The starting cell density after inoculation is ~2 mg of dry weight× $ml^{-1}$. Media are inoculated from cultures pregrown in 80 ml of YPX medium (1% yeast extract, 2% peptone, 8% xylose) at cultivation in 300-ml flasks with shaking at 220 rpm until middle-exponential growth phase. Cells for inoculation are harvested by centrifugation, washed with water and concentrated to achieve the starting density mentioned above.

Those skilled in the art will recognize that other media may be used depending on the growth conditions desired and on the composition of the lignocellulosic material to be used as a raw material for the fermentation.

Enzymes, Primers, and Chemicals

A fragment containing the ORF of the HpHSP104 was isolated by PCR from genomic DNA of the strain CBS 4732 leu2-2 using primers A29: 5'-CCCCATATGGATCAATCA-CAATTTACCGACAGAGC-3' (SEQ ID NO: 1) and A30: 5'-GAACGGCCGCTCAGTCCAAATCTGGAG-3' (SEQ ID NO: 2). Restriction sites NdeI and NotI were incorporated into the primers A29 and A30, respectively, to provide correct orientation of the isolated PCR fragment (the HpHSP104 ORF) into the corresponding site of the plasmid pKO8-GAPpr (description and linear scheme of the plasmid: see the article Voronovsky A. Y. et al., "Expression of xylA Genes Encoding Xylose Isomerases From *Escherichia coli* and *Streptomyces coelicolor* in the Methylotrophic Yeast *Hansenula polymorpha*" FEMS Yeast Res. 5(11): 1055-62 (2005)). Restriction enzymes, DNA modifying enzymes, and other reagents were obtained from New England Biolabs, USA, Sigma, USA and Fermentas, Lithuania.

Reaction conditions employed were as recommended by the suppliers. Genomic DNA of *H. polymorpha* was isolated using the Wizard® Genomic DNA Purification Kit (Promega, USA). Restriction endonucleases and DNA ligase (Fermentas, Lithuania and New England Biolabs, USA) were used according to the manufacturer specifications. Plasmid isolation from *E. coli* was performed with the Wizard® Plus SV Minipreps DNA Purification System (Promega, USA). DNA fragments were separated on 0.8% agarose (Fisher Scientific, USA) gel in 1×TAE (Sambrook et al. Molecular Cloning: A Laboratory Manual. Cold Spring Harbor Laboratory, Cold Spring Harbor, N.Y. 1989.). Isolation of fragments from gel was carried out with the DNA Gel Extraction Kit (Millipore, USA). Amplification of HSP 104 ORFs and HpGAP promoter was done with Platinum® Taq DNA Polymerase High Fidelity (Invitrogen, USA) according to the manufacturer specification. PCRs were performed in GeneAmp® PCR System 9700 thermocycler (Applied Biosystems, USA). With the benefit of this disclosure, those skilled in the art will recognize that the transformations and isolations may be performed with any of a variety of known materials and methods.

Transformation

Those skilled in the art will recognize that a number of methods for transformation of *H. polymorpha* exist. For example, one may use the electroporation method reported in (Faber, K. N., et al., "Highly-efficient Electrotransformation of the Yeast *Hansenula polymorpha*" Curr. Genet. 25: 305-310 (1994)). Transformation using intact cells may also be effective (Roggenkamp R. et al., "Transformation of the methylotrophic yeast *Hansenula polymorpha* by autonomous replication and integration vectors" Mol. Gen. Genet. 202: 302-308 (1986)).

Plasmid Construction

Recombinant plasmids carrying *H. polymorpha* HSP104 ORF driven by the *H. polymorpha* glyceraldehyde-3-phosphate dehydrogenase (GAPDH) promoter (GenBank #AY550078), and also including the *Saccharomyces cerevisiae* LEU2 gene, isolated from the Yep13 plasmid, were constructed on the basis of the plasmid pKO8-GAPpr (Voronovsky A. Y. et al., "Expression of xylA Genes Encoding Xylose Isomerases From *Escherichia coli* and *Streptomyces coelicolor* in the Methylotrophic Yeast *Hansenula polymorpha*" FEMS Yeast Res. 5(11): 1055-62 (2005)). Construction of the plasmid pKO8-GAPpr is reported therein.

The plasmid pKO8+prGAP+HSP104Hp (FIG. 1) was linearized by BamH I and used for transformation of *H. polymorpha* cells of the strain NCYC 495 leu1-1. this allowed us to isolate Leu$^+$ integrants containing the recombinant HpHSP 104 ORF driven with the HpGAPDH promoter.

The recombinant plasmid pΔATH1Hp was used for deletion of the *H. polymorpha* ATH1 gene in the NCYC 495 leu1-1 strain, resulting in creation of the Δath1-36 strain.

Ethanol Assay

The "Alcotest" kit (Gonchar, M. V., Maidan, M. M., Sibirny, A. A. "A new oxidase-peroxidase kit "Alcotest" for ethanol assays in alcoholic beverages" Food Technol Biotechnol. 39: 37-42 (2001)) was used for ethanol assays.

EXAMPLES

The following examples are intended to guide those skilled in the art in the practice of this invention. They should not be construed to limit the scope of the invention, which is defined by the claims.

Example 1

Example 1 describes production of *H. polymorpha* transformants carrying the integrated recombinant HpHSP104. The sequence of the *H. polymorpha* HSP104 gene (HpHSP104), which encodes heat shock protein 104, was obtained from the *H. polymorpha* genome database (Rhein Biotech GmbH). A 2.685 kb fragment containing the ORF of HpHSP104 was isolated by PCR from the genomic DNA of the strain CBS 4732 leu2-2 using primers A29 5'-

(SEQ ID NO: 1)
CCCCATATGGATCAATCACAATTTACCGACAGAGC-3'
and A30

(SEQ ID NO: 2)
5'-GAACGGCCGCTCAGTCCAAATCTGGAG-3'.

Resulting PCR product (the ORF of HpHSP104) was treated with restriction endonucleases NdeI and NotI flanking the product. The NdeI/NotI 2.685 kb-PCR product was ligated with the NdeI/NotI-linearized plasmid pKO8-GAPpr. It resulted in the construct pKO8+prGAP+HSP104Hp. The construct contains the ORF of HpHSP104 driven with the *H. polymorpha* GAPDH promoter (GenBank #AY550078). In addition, pKO8+prGAP+HSP104Hp contains the *Saccharomyces cerevisiae* LEU2 gene (ScLEU2).

The plasmid pKO8+prGAP+HSP104Hp was used for the transformation of the *H. polymorpha* strain NCYC 495 leu1-1 by electroporation.

Integrants containing both ScLEU2 and the recombinant HpHSP104 gene were selected among resulting Leu$^+$ transformants. It was done by PCR using genomic DNA of the transformants as a template and corresponding primers for the promoter GAPDH and 3'-end of HpHSP104 ORF (forward primer A58 5'-CGCGAGCTCCCAATTATCAT-TAATAATCAC-3' (SEQ ID NO: 3) and back primer A30 5'-GAACGGCCGCTCAGTCCAAATCTGGAG-3' (SEQ ID NO: 2).) and ScLEU2 (forward primer IS25: CGGCTGCAG-GAGAACTTCTAGTATATCTACATAC (SEQ ID NO: 4) and back primer IS26: TATCTGCAGCTACGTCGTTAAGGC-CGTTTCTG (SEQ ID NO: 5)). The recombinants were isolated as a result of the work.

Example 2

Example 2 reports tests of thermotolerance and ethanol production in *H. polymorpha* transformants produced in Example 1. The transformants were grown in YNB medium with 12% xylose as carbon source with restricted aeration (140 rpm) at 50° C. Table 2 includes a comparison of thermotolerance of the transformants compared to that of NCYC 495 leu1-1. Table 3 includes a comparison of the ethanol production of the transformants compared to that of NCYC 495 leu1-1 at 50° C.

TABLE 3

Ethanol production (mg/ml) with the *H. polymorpha* transformants carrying the integrated recombinant HpHSP104 gene; YNB medium, 12% xylose; 50° C.

| Day | HSP104-8 | Leu (control) |
|---|---|---|
| 1 | 0.87 | 0.26 |
| 2 | 0.9 | 0.185 |
| 3 | 0.87 | 0.111 |
| 4 | 0.44 | 0.003 |
| 5 | 0.38 | 0.003 |

Example 3

Example 3 describes production of *H. polymorpha* transformants in which the ATH1 (acid trehalase) gene has been partially deleted. 2.507 kb of the ATH1 ORF was deleted by transformation of the NCYC 495 leu1-1 strain with ATH1 deletion cassette; the cassette was amplified from the ΔATH1Hp plasmid using primers: A41 CCCAAGCT-TATACCTTCACTAACATACCAGTGGAC (SEQ ID NO: 6) and A44 CGGGTCGACTCTCTGCGACATAATAAGCTG (SEQ ID NO: 7).

Example 4

Example 4 reports tests of thermotolerance and ethanol production in *H. polymorpha* transformants produced in Example 3. Table 4 includes a comparison of thermotolerance of the transformants compared to that of NCYC 495 leu1-1. Table 5 includes a comparison of the ethanol production of the transformants compared to that of NCYC 495 leu1-1 at 50° C.

TABLE 5

Ethanol production (mg/ml) with the *H. polymorpha* transformants possessing an inactive HpATH1 gene; YNB medium, 12% xylose; 50° C.:

| Day | Δath1-36 | Leu (control) |
|---|---|---|
| 1 | 0.9 | 0.26 |
| 2 | 0.9 | 0.185 |
| 3 | 0.79 | 0.111 |
| 4 | 0.44 | 0.003 |
| 5 | 0.44 | 0.003 |

Example 5

Example 5 describes production of *H. polymorpha* transformants carrying an integrated recombinant HpXYL3 gene and possessing an inactive HpATH1 gene.

Δath1-36 was used as the recipient strain for the transformation with the plasmid pGLG61+prGAP+XYL3Hp. Integrants containing the recombinant HpXYL3 gene were selected among resulting genetecin resistant transformants. It was done by PCR using genomic DNA of the transformants as a template and corresponding primers for promoter GAPDH and recombinant HpXYL3 (forward A58 5'-CGC-GAGCTCCCAATTATCATTAATAATCAC-3' (SEQ ID NO: 2) and back K9 5'-TTTGCGGCCGCTTAA-GACTCTAATTTTTG-3' (SEQ ID NO: 8). 2.507 kb of the ATH1 ORF was deleted by transformation of the NCYC 495 leu1-1 strain with ATH1 deletion cassette; the cassette was amplified from the ΔATH1Hp plasmid using primers: A41 CCCAAGCTTATACCTTCACTAACATACCAGTGGAC (SEQ ID NO: 6) and A44 CGGGTCGACTCTCTGCGA-CATAATAAGCTG (SEQ ID NO: 7).

Whereas particular embodiments of this invention have been described for purposes of illustration, it will be evident to those persons skilled in the art that numerous variations of the details of the present teaching may be made without departing from the invention as defined in the appended claims. Those patents and publications discussed herein should be viewed as indicative of the level of skill in the art, though no admission is made that any document is a prior art reference.

The present teaching describes several different features and aspects of the invention with reference to various exemplary embodiments. It is understood, however, that the invention embraces numerous alternative embodiments, which may be accomplished by combining any of the different features and aspects described herein in any combination that one of ordinary skill in the art would find useful. All of the foregoing patents and publications herein are hereby incorporated by reference. To the extent that the incorporated material conflicts with existing definitions, statements, or other disclosure material set forth in this description, the disclosure as explicitly set forth herein supersedes any conflicting material incorporated by reference.

We claim:

1. An isolated ethanol-producing yeast of the species *Hansenula polymorpha*, wherein the yeast comprises at least one modification selected from the group consisting of:

(a) an inactive ATH1 (acid trehalase) gene;

(b) overexpression of the *H. polymorpha* protein xylulokinase (XYL3) when compared to a parent strain; and (c) overexpression of the *H. polymorpha* protein heat-shock protein 104 when compared to a parent strain.

2. The yeast of claim 1, wherein said yeast comprises an inactive ATH1 gene.

3. The yeast of claim 1, wherein ethanol is produced by said yeast in a medium containing D-xylose as the primary carbon source in amounts larger and/or yield greater than that produced by a parental *H. polymorpha* strain.

4. The yeast of claim 1, wherein said yeast comprises the *H. polymorpha* xylulokinase (XYL3) gene in a higher copy number than a control strain.

5. The yeast of claim 1, wherein said yeast comprises at least one XYL3 gene under the control of a non-native promoter.

6. The yeast of claim 5, wherein said non-native promoter comprises a *H. polymorpha* glyceraldehyde-3-phosphate dehydrogenase (GAPDH) promoter.

7. The yeast of claim 1, wherein said yeast overexpresses *H. polymorpha* xylulokinase when compared to a parent strain, wherein ethanol is produced by said yeast in a medium containing D-xylose as the primary carbon source in amounts larger and/or yields greater than that produced by a parental *H. polymorpha* strain.

8. The yeast of claim 1, wherein said yeast overexpresses *H. polymorpha* protein heat-shock 104 protein when compared to a parent strain, wherein ethanol is produced by said yeast in a medium containing D-xylose as the primary carbon source in amounts larger and/or yields greater that that produced by a parental *H. polymorpha* strain.

9. A strain of *H. polymorpha* deposited as NRRL Y-50061.

* * * * *

SEQUENCE LISTING

<160> NUMBER OF SEQ ID NOS: 8

<210> SEQ ID NO 1
<211> LENGTH: 35
<212> TYPE: DNA
<213> ORGANISM: artificial sequence
<220> FEATURE:
<223> OTHER INFORMATION: pcr primer

<400> SEQUENCE: 1
ccccatatgg atcaatcaca atttaccgac agagc                35

<210> SEQ ID NO 2
<211> LENGTH: 27
<212> TYPE: DNA
<213> ORGANISM: artificial sequence
<220> FEATURE:
<223> OTHER INFORMATION: pcr primer

<400> SEQUENCE: 2
gaacggccgc tcagtccaaa tctggag                27

<210> SEQ ID NO 3
<211> LENGTH: 30
<212> TYPE: DNA
<213> ORGANISM: artificial sequence
<220> FEATURE:
<223> OTHER INFORMATION: pcr primer

<400> SEQUENCE: 3
cgcgagctcc caattatcat taataatcac                30

<210> SEQ ID NO 4
<211> LENGTH: 34
<212> TYPE: DNA
<213> ORGANISM: artificial sequence
<220> FEATURE:
<223> OTHER INFORMATION: pcr primer

<400> SEQUENCE: 4
cggctgcagg agaacttcta gtatatctac atac                34

<210> SEQ ID NO 5
<211> LENGTH: 32

-continued

```
<212> TYPE: DNA
<213> ORGANISM: artificial sequence
<220> FEATURE:
<223> OTHER INFORMATION: pcr primer

<400> SEQUENCE: 5
tatctgcagc tacgtcgtta aggccgtttc tg                                    32

<210> SEQ ID NO 6
<211> LENGTH: 35
<212> TYPE: DNA
<213> ORGANISM: artificial sequence
<220> FEATURE:
<223> OTHER INFORMATION: pcr primer

<400> SEQUENCE: 6
cccaagctta taccttcact aacataccag tggac                                 35

<210> SEQ ID NO 7
<211> LENGTH: 30
<212> TYPE: DNA
<213> ORGANISM: artificial sequence
<220> FEATURE:
<223> OTHER INFORMATION: pcr primer

<400> SEQUENCE: 7
cgggtcgact ctctgcgaca taataagctg                                       30

<210> SEQ ID NO 8
<211> LENGTH: 29
<212> TYPE: DNA
<213> ORGANISM: artificial sequence
<220> FEATURE:
<223> OTHER INFORMATION: pcr primer

<400> SEQUENCE: 8
tttgcggccg cttaagactc taatttttg                                        29
```